United States Patent
Goshen

(10) Patent No.: US 10,878,544 B2
(45) Date of Patent: Dec. 29, 2020

(54) IMAGE DATA PROCESSING

(71) Applicant: KONINKLIJKE PHILIPS N.V., Eindhoven (NL)

(72) Inventor: Liran Goshen, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 460 days.

(21) Appl. No.: 14/353,358

(22) PCT Filed: Oct. 29, 2012

(86) PCT No.: PCT/IB2012/055967
§ 371 (c)(1),
(2) Date: Apr. 22, 2014

(87) PCT Pub. No.: WO2013/064958
PCT Pub. Date: May 10, 2013

(65) Prior Publication Data
US 2014/0270452 A1   Sep. 18, 2014

Related U.S. Application Data

(60) Provisional application No. 61/555,211, filed on Nov. 3, 2011.

(51) Int. Cl.
*G06T 5/50* (2006.01)
*G06T 3/40* (2006.01)
(Continued)

(52) U.S. Cl.
CPC ............ *G06T 5/50* (2013.01); *A61B 6/032* (2013.01); *A61B 6/037* (2013.01); *A61B 6/486* (2013.01); *A61B 6/507* (2013.01); *A61B 6/5205* (2013.01); *A61B 6/5217* (2013.01); *A61B 6/5235* (2013.01); *A61B 6/542* (2013.01);
(Continued)

(58) Field of Classification Search
None
See application file for complete search history.

(56) References Cited

U.S. PATENT DOCUMENTS 5,253,171 A * 10/1993 Hsiao .................... G06T 11/006
378/10
5,937,083 A * 8/1999 Ostuni ......................... 382/131
(Continued)

FOREIGN PATENT DOCUMENTS

CN    102063728 A    5/2011
JP    2004040422 A    2/2004

OTHER PUBLICATIONS

Griffeth L. Use of PET/CT scanning in cancer patients: technical and practical considerations. Baylor University Medical Center Proceedings [serial online]. 2005;(4):321.*
(Continued)

*Primary Examiner* — Jiangen Sun
(74) *Attorney, Agent, or Firm* — Larry Liberchuk

(57) ABSTRACT

An image data processor (116) includes a high resolution restorer (218) configured to restore a voxel neighborhood of a voxel in first image data to a higher resolution, generating restored higher resolution image data, based on a corresponding voxel neighborhood of second higher resolution image data, wherein the second higher resolution image data has higher resolution than the first image data.

15 Claims, 8 Drawing Sheets

Figure 1:
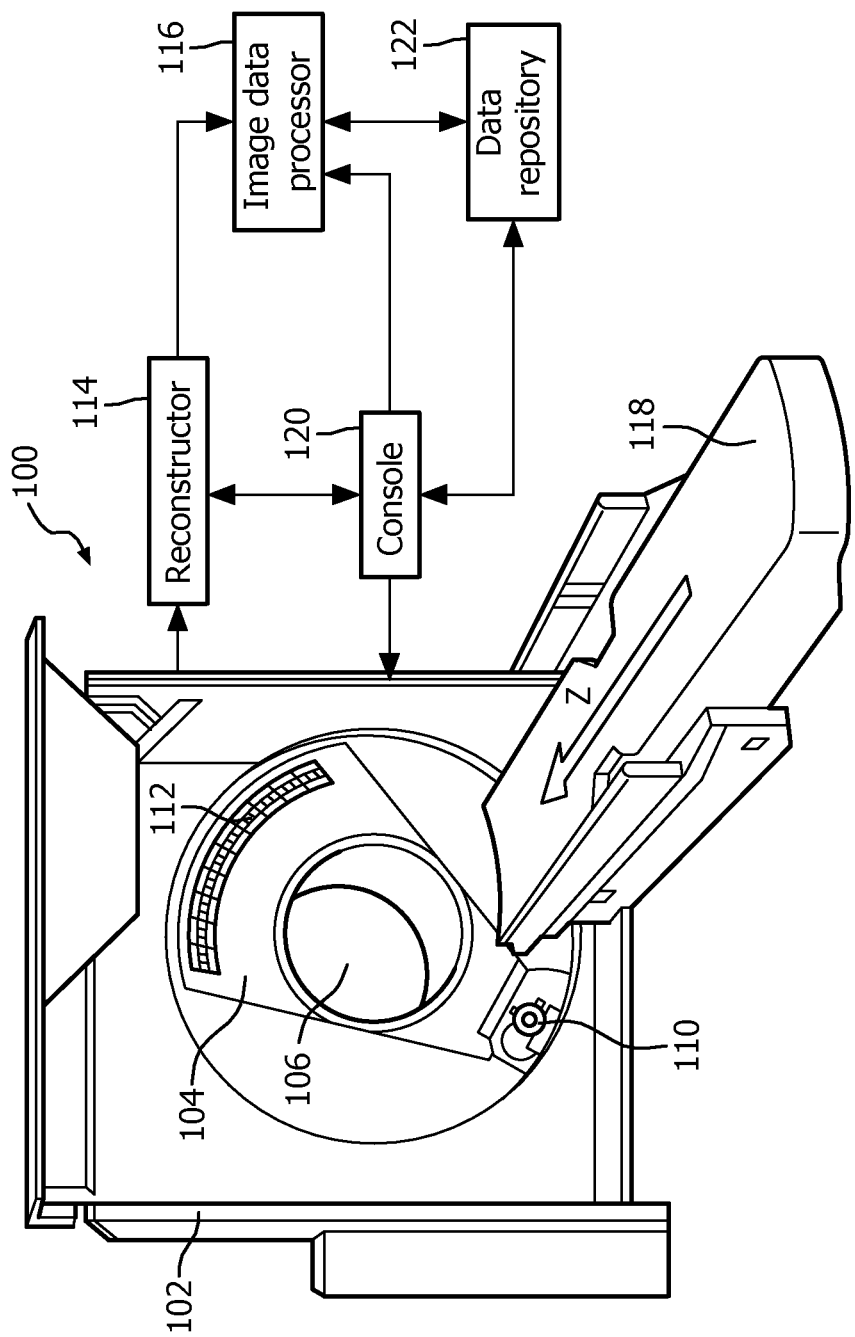

(51) Int. Cl.
*A61B 6/00* (2006.01)
*A61B 6/03* (2006.01)
*G06T 5/00* (2006.01)

(52) U.S. Cl.
CPC ............ *G06T 3/4053* (2013.01); *G06T 5/001* (2013.01); *G06T 2207/10081* (2013.01); *G06T 2207/10104* (2013.01)

(56) References Cited

U.S. PATENT DOCUMENTS

| | | | |
|---|---|---|---|
| 7,447,341 B2 | 11/2008 | Karau | |
| 8,019,169 B2 | 9/2011 | Kondo | |
| 8,098,962 B2 | 1/2012 | Takeshima | |
| 8,264,565 B2 | 9/2012 | Sakaguchi | |
| 8,586,932 B2* | 11/2013 | Rousso et al. | 250/363.04 |
| 8,705,828 B2* | 4/2014 | Yang et al. | 382/131 |
| 2007/0013595 A1 | 1/2007 | Hart et al. | |
| 2009/0226067 A1* | 9/2009 | Souza | G06T 5/005 382/131 |
| 2010/0303358 A1* | 12/2010 | Acharyya | 382/190 |
| 2011/0164799 A1 | 7/2011 | Miao et al. | |
| 2014/0193336 A1* | 7/2014 | Rousso et al. | 424/1.65 |

OTHER PUBLICATIONS

Berliner et al: "Supoer-Resolution Variable-Dose Imaging in Digital Radiography: Quality and Dose Reduction With a Flyoroscopic Flat-Panel Detector"; Int J. Cars (2011) 6:663-673.

Bhat et al: "Using Photographs to Enhance Videos of a Static Scene", Eurographics Symposium on Rendering Techniques, 2007, pp. 327-338.

Kong et al: "Video Super-Resolution With Scene-Specific Priors"; Proceedings of the British Machine Vision Conference, 2006, pp. 549-558.

Schubert et al: "Combining High-Resolution Images With Low-Quality Videos"; Proceedings of the British Machine Vision Conference, Sep. 2008, pp. 1-10.

Liu et al: "A Super Resolution Technique for Clinical Multislice CT" Proc. SPIE 7622, Medical Imaging 2010: Physics of Medical Imaging, vol. 7622, Mar. 2010, pp. 76221Q-1-7622IQ-7.

Tosic et al: "Ultrasound Tomography With Learned Dictionaries": IEEE, ICASSP 2010, pp. 5502-5505.

Liao et al: "Sparse Representations for Limited Data Tomorgraphy": 2008 IEEE, ISBI, pp. 1375-1378.

Freeman, "Example-based super-resolution", IEEE Computer Graphics and Applications, IEEE Service Center, New York, NY, US, vol. 22, No. 2, Mar. 1, 2003.

P. Suetens: "Ch. 2—Radiology", In: Paul Suetens: "Fundamentals of Medical Imaging—2nd edition", 2009, Cambridge University Press, ISBN:978-0-521-51915-1, pp. 14-32.

Howells, "Ch. 13—Principles and Applications of Zone Plate X-Ray Microscope", In: P. Hawkes and J. Spence: "Science of Microscopy", 2007, Springer, ISBN: 0-387-25296-7, pp. 835-926.

"pixel"; "voxel", In: Douglas A. Downing et al.: "Dictionary of Computer and Internet terms—10th edition", 2009, Barron's.

* cited by examiner

IMAGE DATA PROCESSING

CROSS-REFERENCE TO PRIOR APPLICATIONS

This application is the U.S. National Phase application under 35 U.S.C. § 371 of International Application No. 2012/IB2012/055967, filed on Oct. 29, 2012, which claims the benefit of U.S. Provisional Patent Application No. 61/555,211, filed on Nov. 3, 2011. These applications are hereby incorporated by reference in their entirety herein.

The following generally relates to processing image data and is described with particular application to computed tomography (CT) and more particularly to processing reconstructed image data corresponding to a conventional scan and/or a lower dose scan to increase a resolution of the image data; the following is also amenable to other imaging modalities.

A CT scanner generally includes an x-ray tube mounted on a rotatable gantry that rotates around an examination region about a longitudinal or z-axis. The x-ray tube emits radiation that traverses the examination region and a subject or object therein. A detector array subtends an angular arc opposite the examination region from the x-ray tube. The detector array includes one or more rows of detectors that are aligned with respect to each other and that extend along the z-axis. The detectors detect radiation that traverses the examination region and the subject or object therein and generate projection data indicative thereof. A reconstructor processes the projection data and reconstructs three-dimensional (3D) volumetric image data indicative thereof. The volumetric image data can be processed to generate one or more images of the examination region, including the portion of the subject or object disposed therein.

Unfortunately, CT scanners emit ionizing radiation, which may increase a risk of cancer to a scanned patient. Generally, the radiation dose deposited in the patient depends on multiple factors, including, but not limited to, tube current (mAs), tube voltage (kVp), pitch/exposure time (for helical scans), slice thickness and spacing (for axial scans), the number of scans in a study, and patient build (e.g., thicker or thinner). The deposited dose can be reduced by decreasing tube current, tube voltage and/or the number of scans, and/or increasing the pitch, slice thickness and/or slice spacing. However, image noise is inversely proportional to radiation dose, and thus reducing radiation dose not only reduces dose but also increases image noise in the acquired data, which is propagated to the image data during reconstruction, reducing image quality (i.e., noisier, less sharp images), which may degrade the diagnostic value of the imaging data.

Image resolution has been improved through super-resolution algorithms. Some super-resolution algorithms exceed the diffraction-limit of the imaging systems, while other super-resolution algorithms provide an improvement over the resolution of the detector. Multiple-frame super-resolution algorithms generally use sub-pixel shifts between multiple low resolution images of the same scene and improve image resolution by fusing or combining multiple low resolution images into a single higher resolution image. Unfortunately, such processing can be complex and time intensive. Learning-based super-resolution algorithms additionally incorporate application dependent priors to infer the unknown high resolution images.

In view of the above, there is an unresolved need for other approaches for reducing patient dose while preserving image quality and/or improving image quality.

Aspects described herein addresses the above-referenced problems and others.

In one aspect, an image data processor includes a high resolution restorer configured to restore a voxel neighborhood of a voxel in first image data to a higher resolution, generating restored higher resolution image data, based on a corresponding voxel neighborhood of second higher resolution image data, wherein the second higher resolution image data has higher resolution than the first image data.

In another aspect, a method includes receiving first image data, receiving second higher resolution image data, and utilizing the second higher resolution image data to restore the first image data to a resolution of the second higher resolution image data, generating restored higher resolution first image data.

In another aspect, a method includes increasing a resolution of low or conventional dose image data based on a mapping between a higher resolution voxel neighborhood and a lower resolution voxel neighborhood, wherein the higher resolution voxel neighborhood corresponds to a voxel neighborhood about a voxel of the low or conventional dose image data being processed and the lower resolution voxel neighborhood corresponds to a downscaled higher resolution voxel neighborhood.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system in connection with an image data processor, which is configured to improve the resolution of image data, allowing for reduced dose scans for a given image quality and/or improved image quality.

Figure 2:
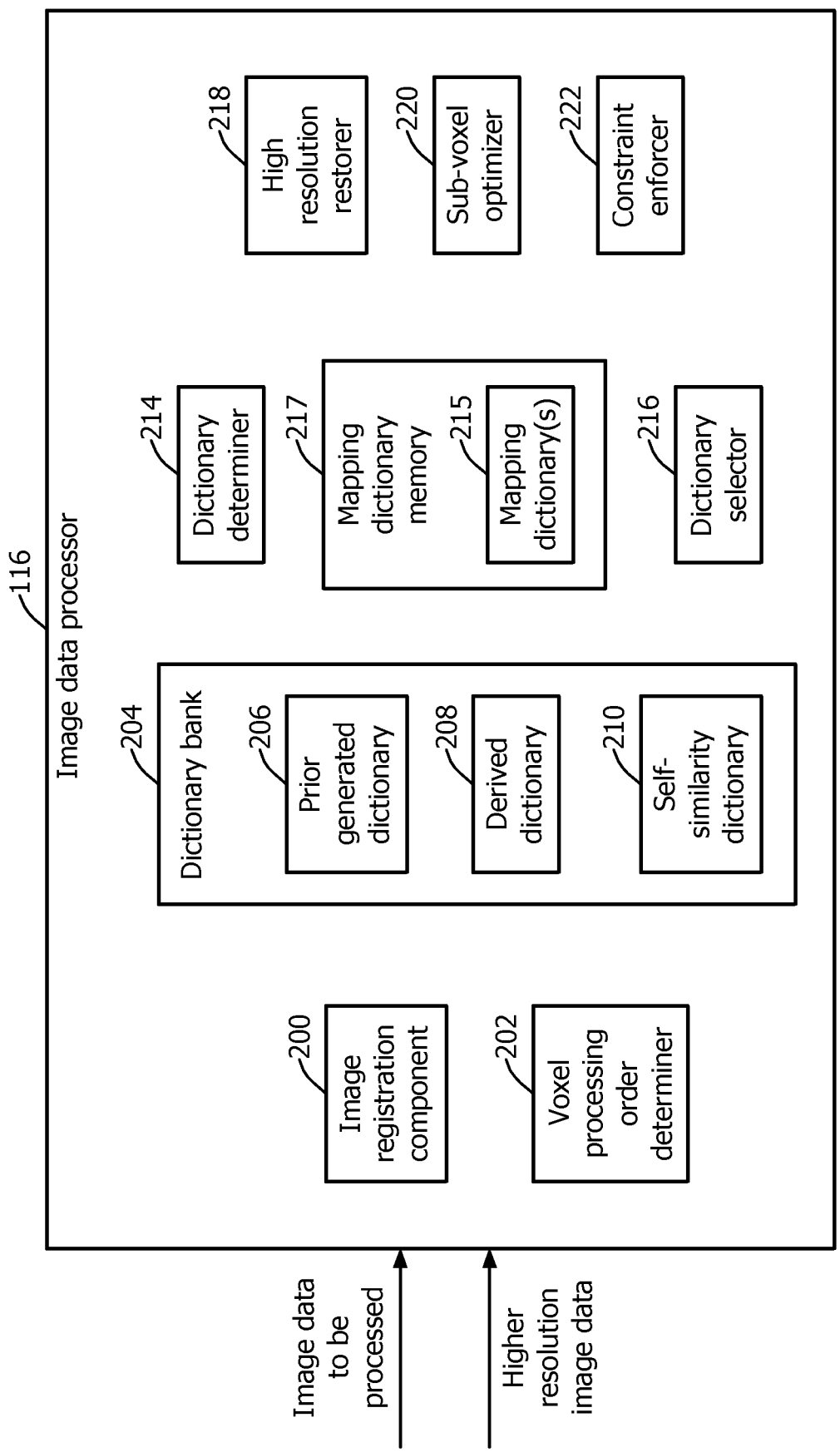

FIG. 2 schematically illustrates an example of the image data processor illustrated in FIG. 1.

Figure 3:
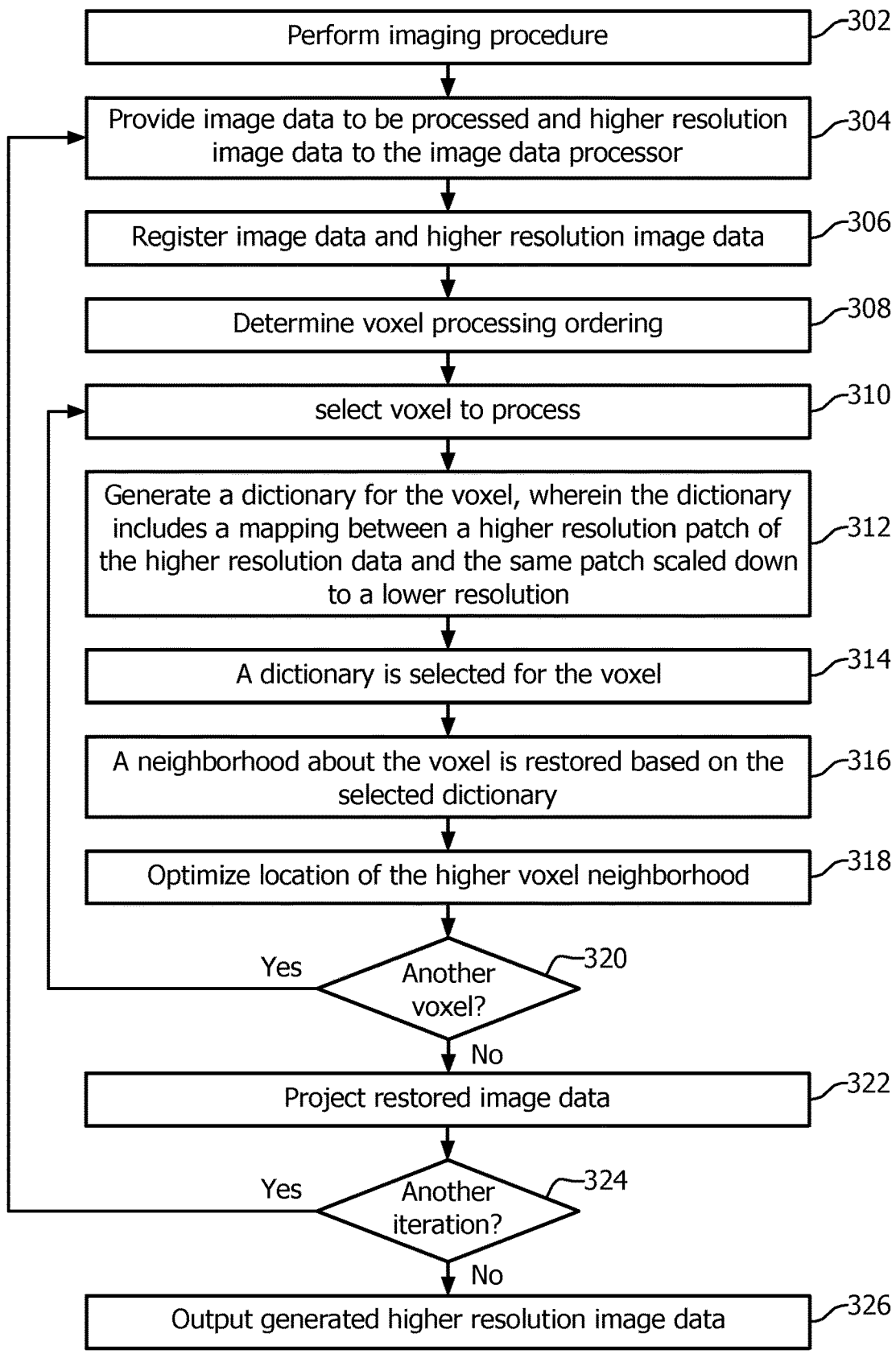

FIG. 3 illustrates an example method for improving the resolution of image data, allowing for reduced dose scans for a given image quality and/or improved image quality.

Figure 4:
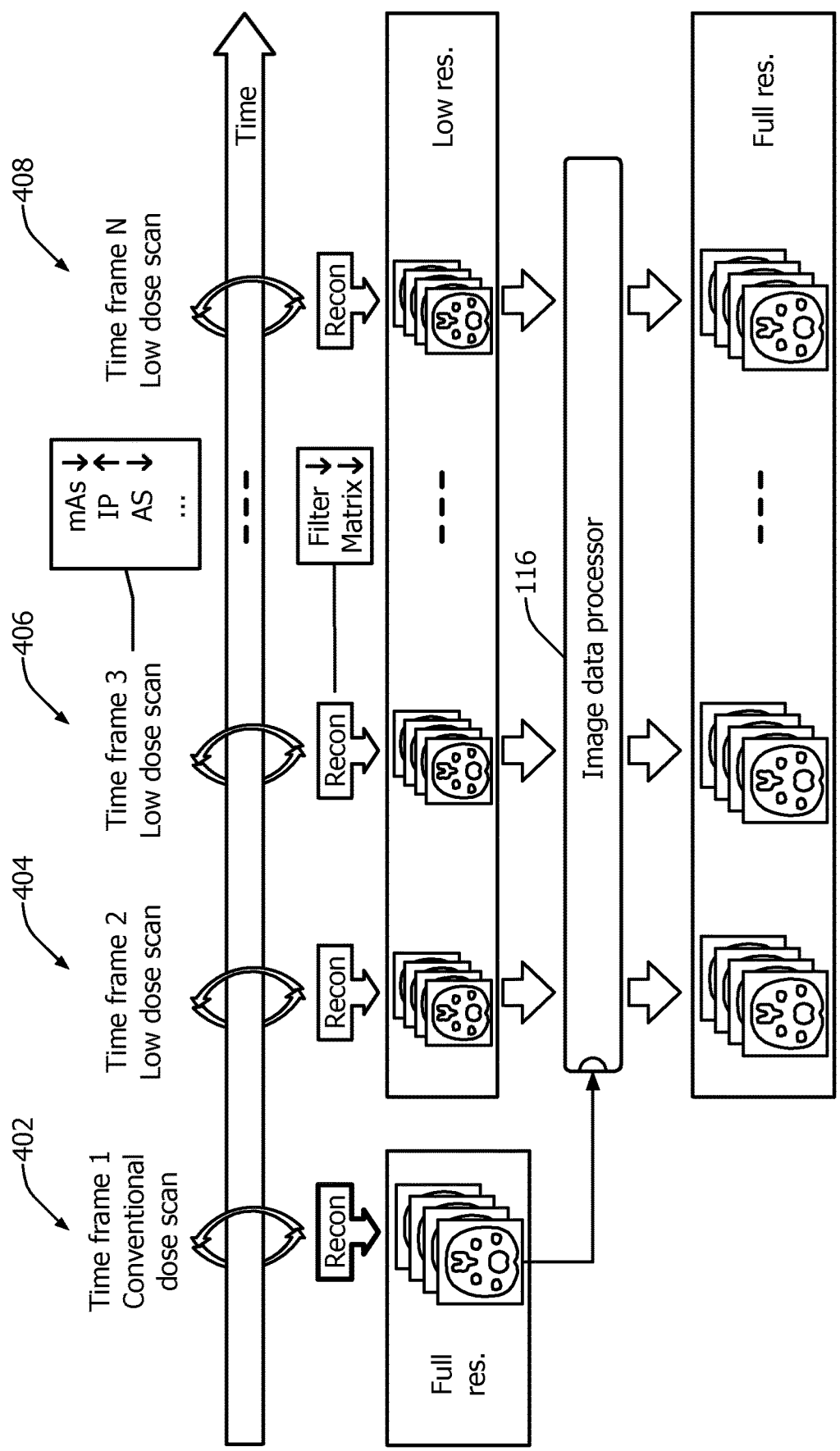

FIG. 4 schematically illustrates an example in which dose is lowered for perfusion imaging.

Figure 5:
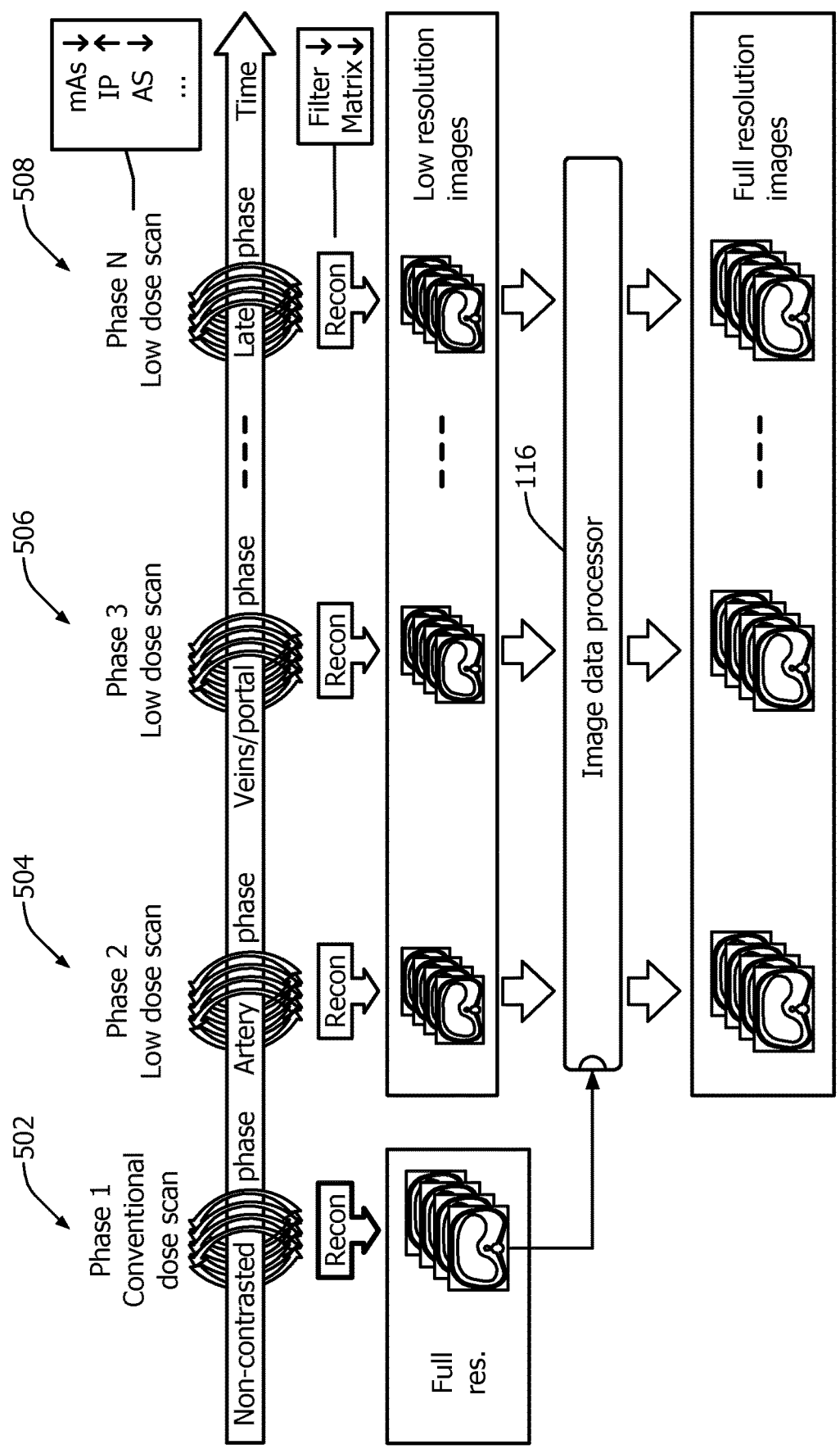

FIG. 5 schematically illustrates an example in which dose is lowered for multi-phasic imaging.

Figure 6:
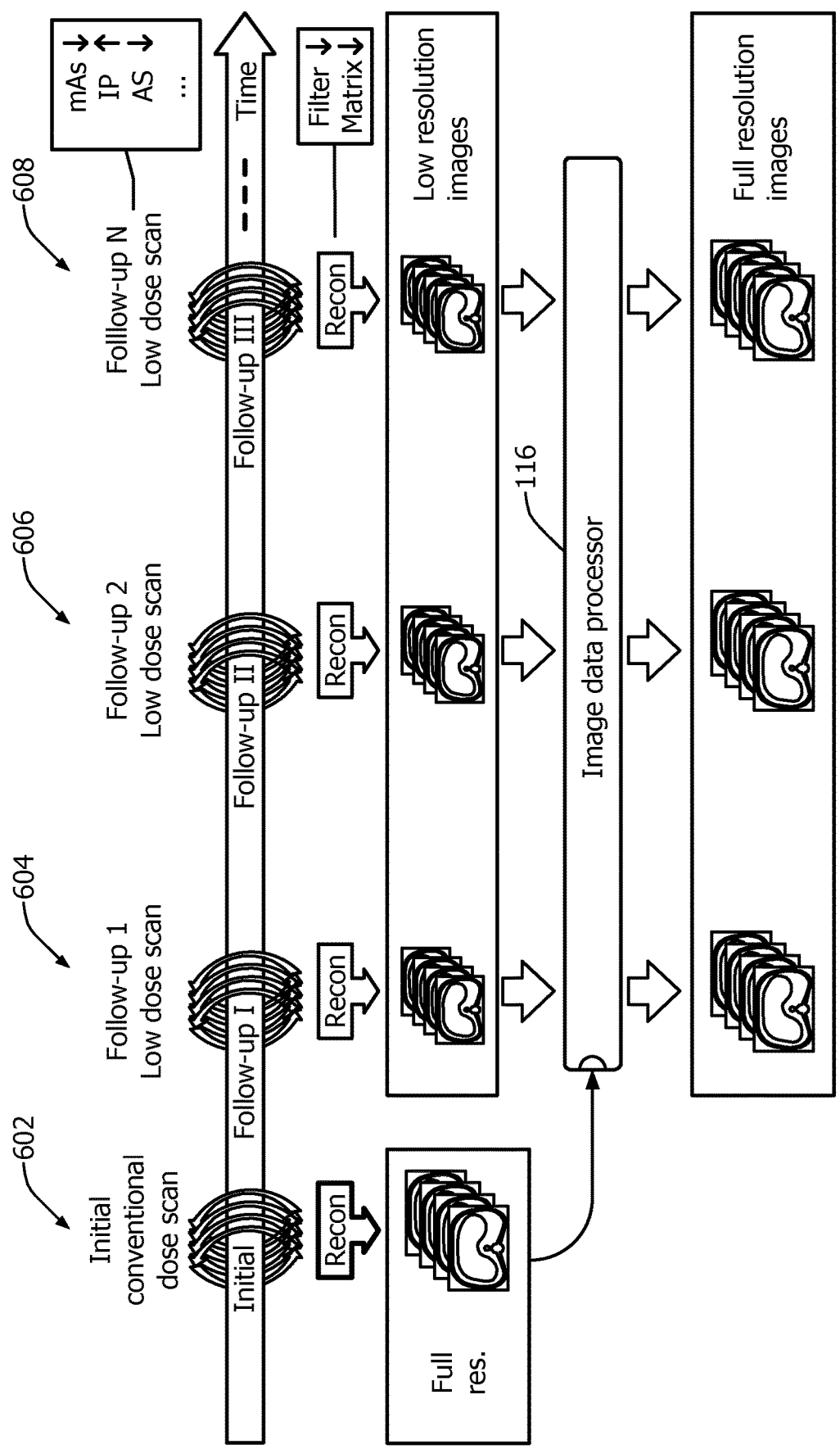

FIG. 6 schematically illustrates an example in which dose is lowered for follow up scans.

Figure 7:
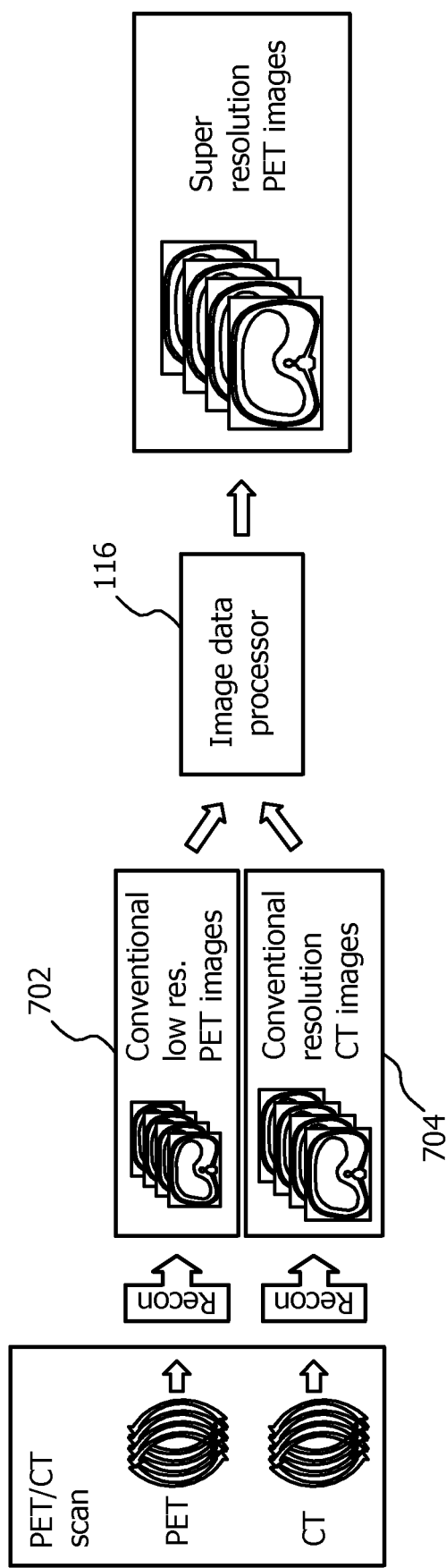

FIG. 7 schematically illustrates an example in which image quality is improved for low dose PET data.

Figure 8:
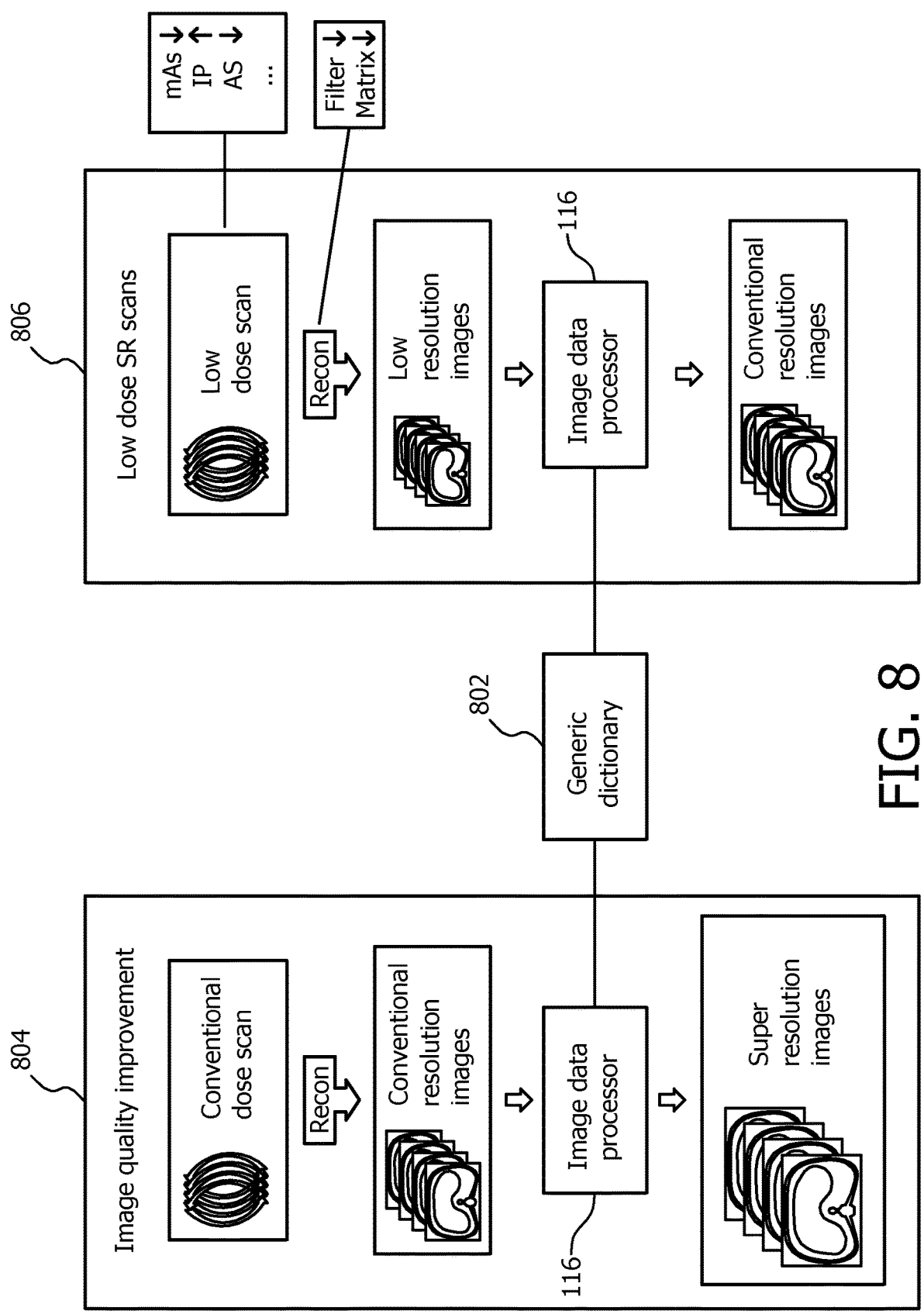

FIG. 8 schematically illustrates an example in which dose is lowered and/or image quality is improved for a scan.

Initially referring to FIG. 1, an imaging system 100 such as a computed tomography (CT) scanner is schematically illustrated. The imaging system 100 includes a generally stationary gantry 102 and a rotating gantry 104. The rotating gantry 104 is rotatably supported by the stationary gantry 102 and rotates around an examination region 106 about a longitudinal or z-axis.

A radiation source 110, such as an x-ray tube, is rotatably supported by the rotating gantry 104. The radiation source 110 rotates with the rotating gantry 104 and emits radiation that traverses the examination region 106. A source collimator includes collimation members that collimate the radiation to form a generally cone, wedge, fan or other shaped radiation beam.

A sensitive detector array 112 subtends an angular arc opposite the radiation source 110 across the examination region 106. The detector array 112 includes a plurality of rows of detectors that extend along the z-axis direction. The detector array 112 detects radiation traversing the examination region 106 and generates projection data indicative thereof.

A reconstructor 114 reconstructs the projection data and generates three-dimensional (3D) volumetric image data indicative thereof. The reconstructor 114 may employ a conventional 3D filtered-backprojection reconstruction, a cone beam algorithm, an iterative algorithm and/or other algorithm.

An image data processor 116 processes image data, generating higher resolution image data. As described in greater detail below, the image data processor 116 employs information obtained from previously generated higher resolution image data to improve image resolution of lower and/or conventional dose image data. In one instance, this allows for reducing patient dose of a study for a given image quality and/or improving the image quality of the study. By way of example, the image data processor 116 allows for dose reduction of perfusion scans, dose reduction of multi-phasic scans (e.g., three phase liver scans), dose reduction of follow-up scans (e.g., follow-up scans for treatment response), image quality improvement of PET data (e.g., spatial resolution enhancement for the PET images), dose reduction and/or image quality improvements of generic scans, and/or other dose reduction and/or image quality improvements for other imaging studies.

A subject support 118, such as a couch, supports an object or subject such as a human or animal patient in the examination region 106. The subject support 118 is configured to move vertically and/or horizontally before, during, and/or after a scan to position the subject or object in connection with the system 100.

A general-purpose computing system or computer serves as an operator console 120. The console 120 includes a human readable output device such as a monitor or display and an input device such as a keyboard, mouse, etc. Software resident on the console 120 allows the operator to interact with the scanner 100 via a graphical user interface (GUI) or otherwise. This interaction may include setting various imaging parameters such as tube current, temporal resolution, angular sampling, image matrix size, back projection filter, etc., selecting an image data resolution improving post-processing algorithm, and/or interaction.

A data repository 122 can be used to store the image data generated by the system 100 and/or the image data processor 116, image data used by the image data processor 116, and/or other data. The data repository 122 may include one or more of a picture archiving and communication system (PACS), a radiology information system (RIS), a hospital information system (HIS), an electronic medical record (EMR) database, a sever, a computer, and/or other data repository. The data repository 122 can be local to the system 100 or remote from the system 100.

It is to be appreciated that the image data processor 116 can be implemented via a processor executing one or more computer readable instructions encoded or embedded on computer readable storage medium such as physical memory. Such a processor can be part of the console 120 and/or other computing device such as a dedicated visualization computer, and/or other computing device. Additionally or alternatively, the processor can execute at least one computer readable instructions carried by a carrier wave, a signal, or other non-computer readable storage medium such as a transitory medium.

FIG. 2 schematically illustrates an example of the image data processor 116.

The illustrated image data processor 116 receives first image data or image data to be processed to increase its resolution and generate higher resolution image data. This image data may be lower dose image data being processed to improve its resolution, for example, to a level of that of conventional dose image data (or lower or higher). Alternatively, the image data may be conventional dose image data being processed solely to increase the resolution. The image data can come from the reconstructor 114 (FIG. 1), the data repository 122 (FIG. 1) and/or other device.

The illustrated image data processor 116 also receives second higher resolution image data, which has a resolution higher than that of the first image data. The higher resolution image data, likewise, can come from the reconstructor 114 (FIG. 1), the data repository 122 (FIG. 1) and/or other device. The second higher resolution image data may correspond to the same patient or a different patient. The second higher resolution image data may alternatively be derived from the first image data.

An image registration component 200 registers the first image data and the second higher resolution image data. This may include matching a voxel neighborhood in the first image data and a voxel neighborhood in the second higher resolution image data. An elastic and/or rigid registration approach can be employed. In another embodiment, the image registration component 200 is omitted, and a default matching scheme is utilized.

A voxel processing order determiner 202 determines a processing ordering of the voxels of the first image data. Example orderings include, but are not limited to, a decreasing order of the voxel gradient magnitude, a decreasing order of a product of structure tensor Eigen values of a neighborhood of the voxel, and/or other ordering. Such orderings may depend on the voxel values, and may vary from image data to image data. In another embodiment, a fixed ordering is utilized. The particular ordering can be automatically selected by the determiner 202 and/or manually based on input provided by a user of the image data processor 116.

A dictionary bank 204 stores various dictionaries, or mappings between groups (e.g., 3×3, 5×5, etc.) of lower resolution voxels and higher resolution voxels. The illustrated dictionary bank 204 includes at least one of a prior generated dictionary 206, a derived dictionary 208 or a self-similarity dictionary 210. The prior generated dictionary 206 includes an already generated dictionary provided to the image data processor 116. A dictionary determiner 212 determines the derived dictionary 208 and/or the self-similarity dictionary 210. The dictionary determiner 214 may have determined the prior generated dictionary 206, for example, during earlier processing of first image data and/or other image data corresponding to the same patient and/or another patient.

The derived dictionary 208 includes a dictionary for each voxel to be processed in the first image data. In one instance, the derivation includes identifying a voxel neighborhood in the second higher resolution image that corresponds to a voxel in the first image data. The result of the registration can be used to identify the voxel neighborhood. The identified voxel neighborhood in the second higher resolution image data is downscaled to a pre-determined lower resolution. The down scaling can be achieved by smoothing and/or other processing with an appropriate filter and, optionally, sub-sampling the filtered higher resolution image data. A dictionary is then derived as a collection of matches between the voxel neighborhoods of second higher resolution image data and the downscaled second higher resolution.

The self-similarity dictionary 210 is similar to the derived dictionary 208 except that the voxel neighborhood of the first image data is downscaled and the dictionary is determined as a collection of matches between the voxel neighborhoods of first image data and the downed scaled first image data. In addition, in this example, the dictionary determiner 214 only collects voxels that are in the neighborhood of the first image data. In another embodiment, other voxels may additionally or alternatively be collected.

The illustrated dictionary determiner 214 combines two or more of the prior generated dictionary 206, the derived dictionary 208 and the self-similarity dictionary 210, creating a mapping dictionary 215, for each voxel, which, in the illustrated embodiment, can be stored in mapping dictionary memory 217. For instance, in this example, the dictionary determiner 214 forms the mapping dictionary for a voxel by aggregating the prior generated dictionary 206, the derived dictionary 208, and the self-similarity dictionary 210 to form a mapping dictionary 215 for the voxel that includes all three of the prior generated, derived dictionary, and the self-similarity dictionaries 206, 208 and 210. Generally, the mapping dictionaries collectively represent a mapping or relationship between matrices of voxels (the voxel neighborhoods).

A dictionary selector 216 selects the corresponding mapping dictionary 215 from the mapping dictionary memory 217 for each voxel of the first image data to be processed. The selection can be done automatically based on default and/or use defined preferences and/or manually based on input provided by the user of the image data processor 116. In one instance, the selection of the mapping dictionary 215 is based on a compatibility of the dictionary of the second higher resolution image data with voxels that were already restored and/or compatibility of the dictionary of the first image data with the voxel neighborhood in the first image data.

A high resolution restorer 218 utilizes the higher resolution voxel neighborhood of the selected mapping dictionary to restore a higher resolution neighborhood around the voxel of the first image data being processed.

An optional sub-voxel optimizer 220 is configured to optimize a location of the higher resolution voxel neighborhood for the voxel being processed. In one instance, this may improve the compatibility of the selected mapping dictionary. The optimization can be achieved by sub-pixel shifts of the selected mapping dictionary and/or otherwise.

A constraint enforcer 222 processes the restored (or the optimized restored) image data to enforce any global restoration constraint between the image data to be processed. This can be achieved using a back-projection and/or other approach. An example suitable back-projection is $I_{t+1}^{high}=I_t^{high}+US(I^{low}-DS(I_t^{high}))$, where $I^{low}$ is the input study, $I_0^{high}$ is the output study of the previous step, US is an up-scaling operator, and DS is a down-scaling operator.

The image data processor 116 may process the first image data using a single pass or an iterative refinement approach in which the output generated higher resolution image data is fed back as input first image data to be processed as discussed above. With the iterative approach, the image data can be processed via one or more iterations. Suitable stopping criteria may include, but is not limited to, a difference between the output of consecutive processing, a number of iterations, a lapse of a pre-determined amount of time, and/or other criteria. The iterative approach may allow for improving, with each iteration or a given set of iterations, the compatibility of the selected mapping dictionary.

FIG. 3 illustrates an example method for improving the resolution of image data low dose and/or conventional dose image data.

It is to be appreciated that the ordering of the acts in the methods described herein is not limiting. As such, other orderings are contemplated herein. In addition, one or more acts may be omitted and/or one or more additional acts may be included.

At 302, an imaging procedure is performed. For example, the imaging system 100 of FIG. 1 can be used to scan an object or subject and generate image data. The scan can be a conventional dose scan or a lower dose scan in which a deposited dose of the lower dose scan is less than a deposited dose of the conventional dose scan.

At 304, image data to be processed (e.g., image data from the scan of act 302) and higher resolution image data (i.e., image data with a higher resolution than the image data form the scan of act 302) is provided to the image data processor 116. The higher resolution image data may correspond to the same or a different object or subject. In addition, the higher resolution image data may have been generated during a conventional or higher dose imaging procedure, or a lower dose imaging procedure where the lower dose imaging data is processed to generate the higher resolution image data.

At 306, the image data and the higher resolution image data are registered or otherwise mapped to each other. As discussed herein, a suitable registration algorithm includes an elastic or a rigid registration algorithm.

At 308, a processing order of the voxels of the image data is determined. As discussed herein, the ordering can be adaptive or fixed, and generally based on the information provided by a voxel.

At 310, a voxel to be processed is identified.

At 312, a mapping dictionary is generated for the voxel. As discussed herein, the mapping dictionary represents a mapping between matrices of corresponding lower and higher resolution voxel neighborhoods of the image data and/or the higher resolution image data, where the lower resolution voxel neighborhood is generated by downscaling the voxel neighborhood.

At 314, a mapping dictionary is selected for the voxel.

At 316, a neighborhood of the voxel being processed is restored to the higher resolution based on the higher resolution voxel neighborhood of the selected mapping dictionary.

At 318, optionally, the location of the higher resolution voxel neighborhood is optimized for the voxel being processed.

At 320, if there are more voxels to process, acts 310 to 318 are repeated.

If not, then at act 322, the restored (or the optionally optimized restored) image data is projected to enforce any global restoration constraint between the image data to be processed and the generated higher resolution image data, as described herein.

At 324, if the image data is to be processed via one or more subsequent iterations, acts 304 to 322 are repeated with the output generated higher resolution image data from act 320 being the input image data to be processed in the nest iteration.

Otherwise, at act 326, the restored (or the optionally optimized restored) image data (i.e., the generated higher resolution image data for the input image data) is output.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The following presents non-limiting example protocols for dose reduction and/or image quality improvement in connection with perfusion scans, multi-phasic scans, follow-up scans, PET/CT scans and generic scans and the system(s) and/or method(s) described herein.

Initially referring to FIG. 4, an example perfusion scan protocol to reduce overall dose is illustrated. In this example, a conventional dose (full resolution) scan is performed for a first time frame 402, and, for each subsequent time frame 404, 406, . . . , 408, a lower dose scan can be performed. The image quality of the image data of each of the subsequent time frames 404-408 is improved via the image data processor 116 as described herein employing the image data of the conventional scan at the first time frame 402 as the higher resolution image data used increase the resolution of the image data of the lower dose scans. It is to be appreciated that the conventional dose scan does not have to be the first scan. In addition, the conventional dose scan can be from a different scan (a scan other than the example perfusion scan), for example, a CTA and/or other scan.

To mitigate any detection limitations associated with low x-ray flux, pre-determined settings can be used. Suitable settings may increase the x-ray flux while compromising the sampling resolution. By way of example, the milliampere seconds (mAs) should be reduced which causes dose reduction and x-ray flux reduction, the integration period (IP) should be increased which causes x-ray flux increase and resolution degradation, the angular sampling (AS) should be reduced as the IP is increased, a single focal spot mode can be used (instead of two or more) which causes x-ray flux increase and resolution degradation, a smaller image matrix can be used because of the resolution degradation, and the back projection filter can be a soft filter because of the resolution degradation.

Next at FIG. 5, an example multi-phasic scan protocol to reduce overall dose is illustrated. With the protocol, a single conventional (full dose) dose scan is performed in the first (e.g., non-contrast) phase of interest 502, and, for each subsequent phase of interest (e.g., artery phase, vein/portal phase, late phase, etc.) 504, 506, . . . , 508, a lower dose scan can be performed. The image quality of the image data at each subsequent phase of interest 504-508 can be improved via the image data processor 116 as described herein employing the image data of the conventional scan at the first phase of interest 502 as the higher resolution data used increase the resolution of the image data of the lower dose scans. As with perfusion protocol, detection limitations associated with low x-ray flux can be mitigated by using appropriate low dose imaging settings. In addition, the conventional dose scan can be performed in a different phase of interest.

Turning to FIG. 6, an example follow up scan protocol to reduce overall dose is illustrated. Likewise, a conventional dose (full resolution) scan is performed in a first scan 602, and, for each subsequent scan 604, 606, . . . , 608, a lower dose scan can be performed. The image quality of the image data at each subsequent scan can be improved via the image data processor 116 as described herein employing the image data of the conventional scan at the first scan 602 as the higher resolution data used increase the resolution of the image data of the lower dose scans. As with perfusion and multi-phasic protocols, detection limitations associated with low x-ray flux can be mitigated by using appropriate low dose imaging settings, and the conventional dose scan can be performed in a follow up scan.

FIG. 7 illustrates an embodiment to improve the spatial resolution of conventional low resolution PET data 702 with conventional resolution CT image data 704 via the image data processor 116 using the CT image data 704 as the image data to increase the resolution of the PET data 702. FIG. 8 illustrates an embodiment in which a generic dictionary 802 is utilized by the image data processor 116 to either improve image quality of conventional dose image data as shown at 804 or lower dose image data as shown at 806. In a variation, both image quality is improved and dose is reduced using the generic dictionary 802.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An image processing device for improving resolution of image data, comprising:
   at least one processor configured to execute instructions; and
   a memory for storing the instructions that, when executed by the at least one processor, configure the image processing device to:
      receive first resolution three dimensional (3D) volumetric image data;
      receive second resolution 3D volumetric image data being greater than the first resolution;
      register the first resolution 3D volumetric image data and the second resolution 3D volumetric image data; and
      identify a voxel in the first resolution 3D volumetric image data;
      identify a voxel neighborhood about the voxel;
      identify a corresponding voxel neighborhood in the second resolution 3D volumetric image data;
      downscale the corresponding voxel neighborhood to generate a downscaled second resolution 3D volumetric image data;
      determine a mapping between a voxel neighborhood of the second resolution 3D volumetric image data and a voxel neighborhood of the downscaled second resolution 3D volumetric image data; and
      directly restore the first resolution 3D volumetric image data to a resolution of the second resolution 3D volumetric image data based on the mapping.

2. The image processing device according to claim 1, wherein the at least one processor is further configured to enforce at least one predetermined global restoration constraint between the first resolution 3D volumetric image data and the restored higher resolution 3D volumetric image data.

3. The image processing device according to claim 1, wherein the at least one processor is further configured to optimize a location of the voxel neighborhood of the second resolution 3D volumetric image data with respect to another voxel neighborhood of the first resolution 3D volumetric image data.

4. The image processing device according to claim 1, wherein the voxel neighborhood of the second resolution 3D volumetric image data is determined based on a mapping dictionary of the voxel, wherein the mapping dictionary includes a plurality of mappings between groups of lower resolution voxels and higher resolution voxels.

5. The image processing device according to claim 4, wherein the mapping dictionary includes at least one of a prior generated dictionary, a derived dictionary, and a self-similarity dictionary.

6. The image processing device according to claim 5, wherein the prior generated dictionary is previously generated based on different 3D volumetric image data.

7. The image processing device according to claim 5, wherein the at least one processor is further configured to determine the derived dictionary from the second resolution 3D volumetric image data for each voxel of the first resolution 3D volumetric image data.

8. The image processing device according to claim 7, wherein the at least one processor is further configured to determine the derived dictionary as a collection of matches between the voxel neighborhoods of the second resolution 3D volumetric image data and of the downscaled second resolution 3D image data.

9. The image processing device according to claim 7, wherein the at least one processor is further configured to determine at least one dictionary based on the registered first and second resolution 3D volumetric image data.

10. The image processing device according to claim 1, wherein the at least one processor is further configured to determine a processing ordering of the voxels of the first resolution 3D volumetric image data based on at least one of a decreasing order of a voxel gradient magnitude and a decreasing order of a product of structure tensor Eigen values of the voxels.

11. The image processing device according to claim 1, wherein the first resolution 3D volumetric image data is a first dose image, and a dose of the second resolution 3D volumetric image data is greater than the dose of the first dose image.

12. The image processing device according to claim 1, wherein the first resolution 3D volumetric image data is CT or PET image data, and the second resolution 3D volumetric data is CT image data.

13. A method for improving resolution of image data, comprising:
    receiving first resolution three dimensional (3D) volumetric image data;
    receiving second resolution 3D volumetric image data being greater than the first resolution;
    registering the first resolution 3D volumetric image data and the second resolution 3D image data;
    identifying a voxel in the first resolution 3D volumetric image data;
    identifying a voxel neighborhood about the voxel;
    identifying a corresponding voxel neighborhood in the second resolution 3D volumetric image data;
    downscaling the corresponding voxel neighborhood to generate a downscaled second resolution 3D volumetric image data;
    determining a mapping between a voxel neighborhood of the second resolution 3D volumetric image data and a voxel neighborhood of the downscaled second resolution 3D volumetric image data; and
    directly restoring the first resolution 3D volumetric image data to a resolution of the second resolution 3D volumetric image data based on the mapping.

14. The method of claim 13, further comprising:
    determining a processing order of the voxels of the first resolution 3D volumetric image data based on at least one of a decreasing order of a voxel gradient magnitude or a decreasing order of a product of structure tensor Eigen values of the voxels.

15. The method of claim 13, wherein the first resolution 3D volumetric image data includes one of low dose perfusion CT image data, low dose multi-phasic CT image data, low dose follow scan CT image data, low dose PET data, low dose CT image data, or conventional dose CT data.

* * * * *